United States Patent

Bour et al.

Patent Number: 6,051,972
Date of Patent: Apr. 18, 2000

[54] EDDY CURRENT INSPECTION OF TUBES WITH MAGNETIC SATURATION BY A CONCENTRATED MAGNET GENERATED MAGNETIC FIELD

[75] Inventors: Denis Bour, Lyon; Stéphane Ducarme, Chalons Sur Saone, both of France

[73] Assignees: Framatome, Courbevoie; Compagnie Generale Des Matieres Nucleaires, Velizy-Villacoublay, both of France

[21] Appl. No.: 08/894,450

[22] PCT Filed: Dec. 24, 1996

[86] PCT No.: PCT/FR96/02080

§ 371 Date: Aug. 19, 1997

§ 102(e) Date: Aug. 19, 1997

[87] PCT Pub. No.: WO97/24611

PCT Pub. Date: Jul. 10, 1997

[30] Foreign Application Priority Data

Dec. 29, 1995 [FR] France .................................. 95 15737

[51] Int. Cl.[7] .................................................. G01N 27/82
[52] U.S. Cl. .......................... 324/238; 324/230; 324/234
[58] Field of Search .......................... 324/228, 229–231, 324/236–241, 338, 234

[56] References Cited

U.S. PATENT DOCUMENTS

| | | |
|---|---|---|
| 3,441,840 | 4/1969 | Randle ..................................... 324/230 |
| 3,760,264 | 9/1973 | Zumbach ................................. 324/230 |
| 3,761,804 | 9/1973 | Steingroever ........................... 324/230 |
| 3,803,482 | 4/1974 | Steingroever ........................... 324/230 |
| 3,922,599 | 11/1975 | Steingroever ........................... 324/230 |
| 3,986,105 | 10/1976 | Nix et al. ................................. 324/230 |
| 5,293,117 | 3/1994 | Hwang .................................... 324/220 |

FOREIGN PATENT DOCUMENTS 2122752   1/1984   United Kingdom ................... 324/230

*Primary Examiner*—Jay Patidar
*Attorney, Agent, or Firm*—Pollock, Vande Sande & Amernick

[57] ABSTRACT

The apparatus enables eddy current inspection of a metal tube having a thin layer on its outside face with magnetic or electrical characteristics that are different from those of the metal in-depth. The apparatus comprises a measurement head having a measurement coil (14) for surrounding the tube and means for powering the coil with voltage at high frequency, greater than 100 kHz, and for analyzing the impedance of the coil. The head contains a magnet (22) surrounding the coil and magnetic flux guides (24) on either side of the coil in the axial direction and co-operating with the magnet to constitute a magnetic circuit that creates a magnetic field whose maximum intensity lies inside the coil and close thereto.

12 Claims, 2 Drawing Sheets

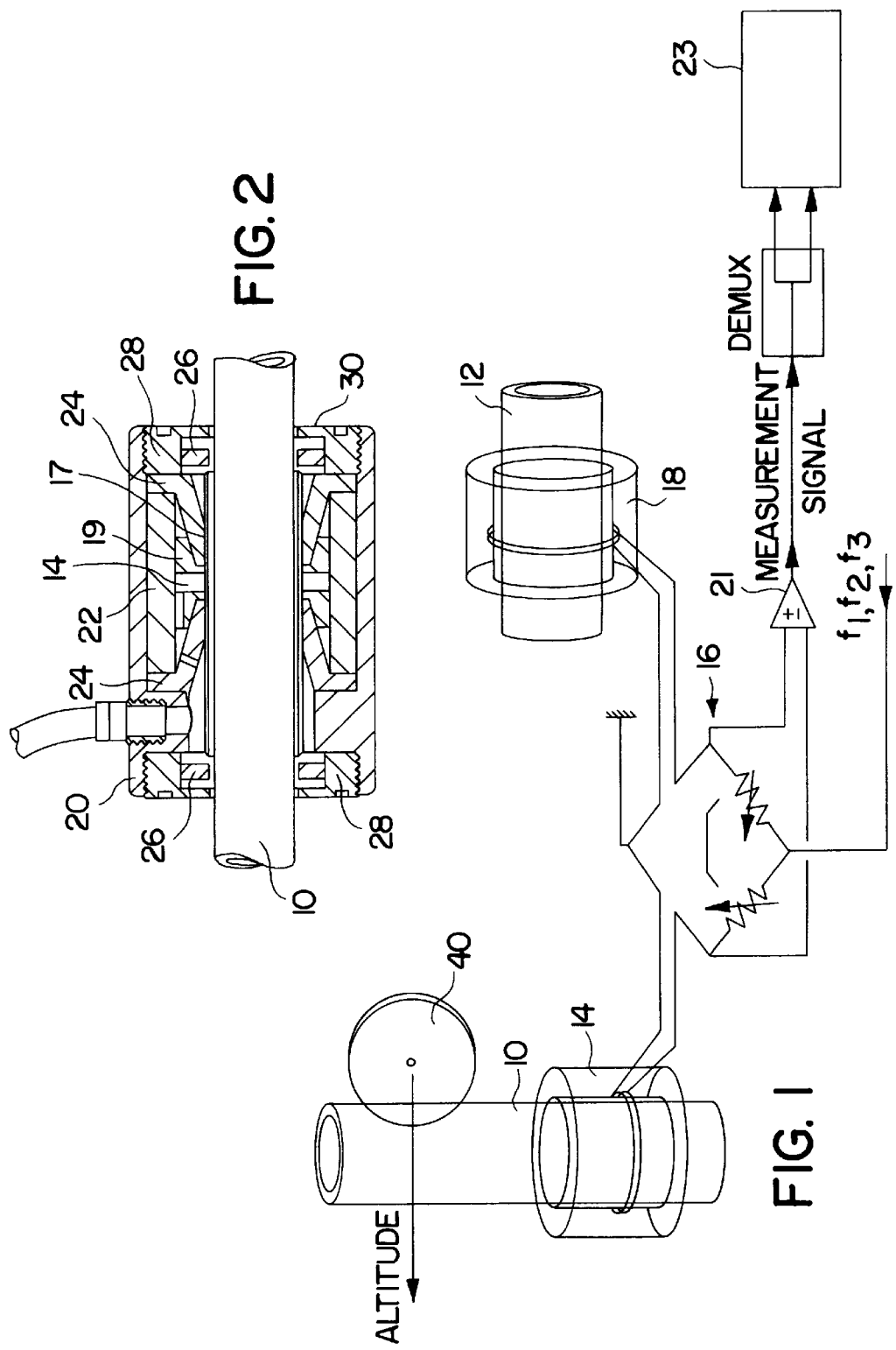
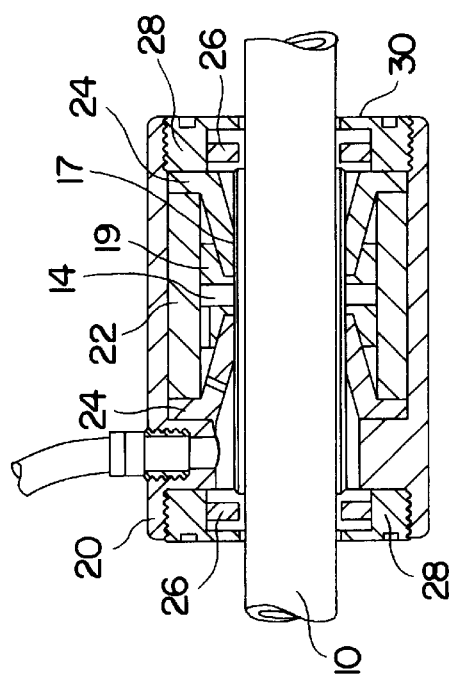

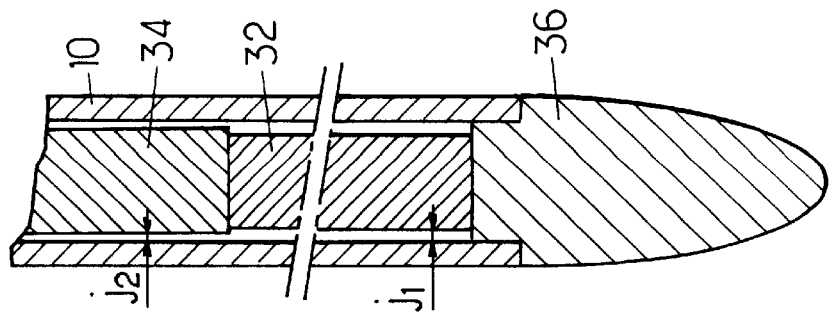
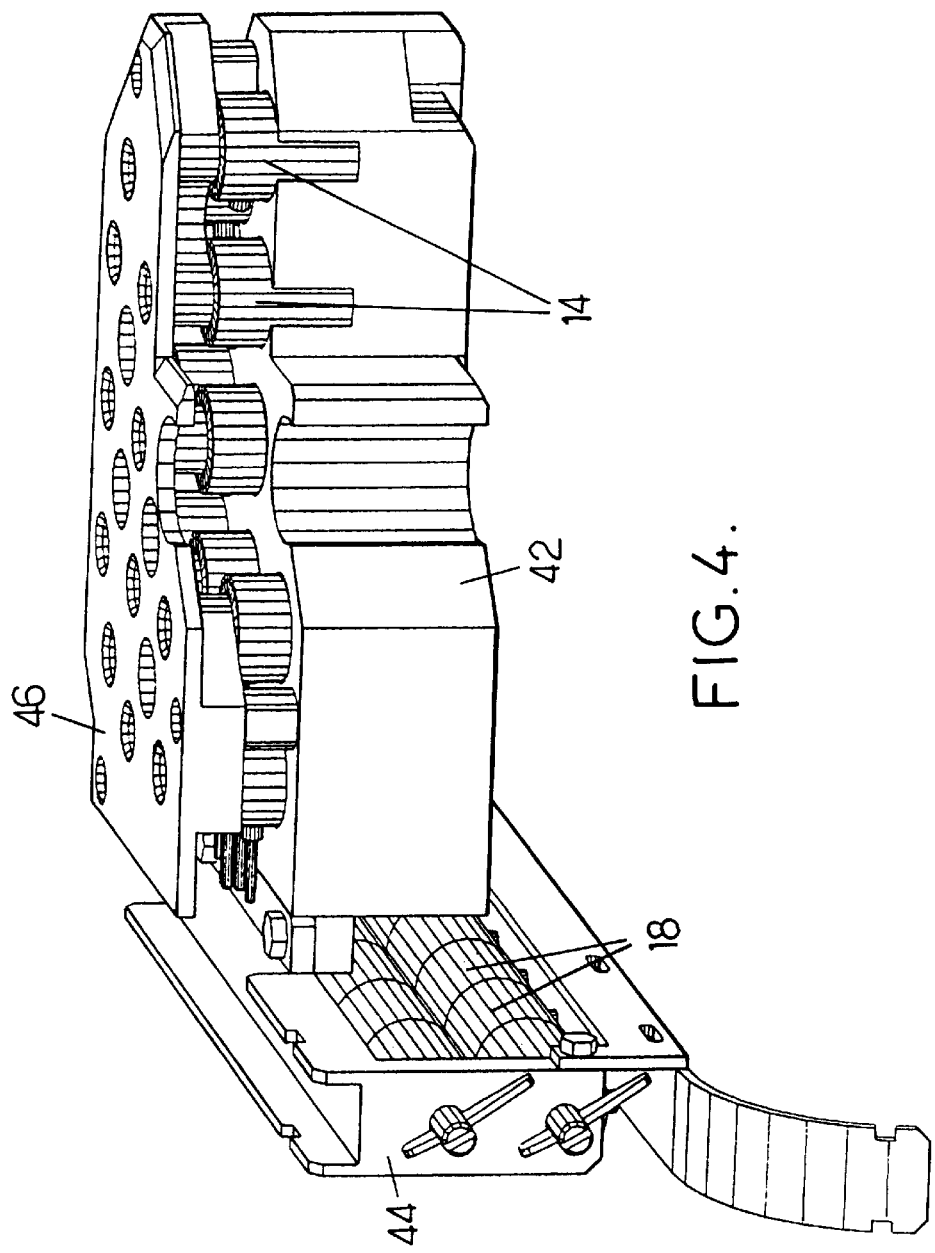

EDDY CURRENT INSPECTION OF TUBES WITH MAGNETIC SATURATION BY A CONCENTRATED MAGNET GENERATED MAGNETIC FIELD

BACKGROUND OF THE INVENTION

The present invention relates to inspecting metal tubes by eddy currents, and a major, although not exclusive, application thereof lies in inspecting the cladding tubes of rods containing a neutron-absorbing material or a fertile material for use in the control clusters of a nuclear reactor.

A method of inspecting the rods of control clusters by eddy currents that is already known (FR-A-2 585 869) corresponding to U.S. Pat. No. 4,741,878 to Gebelin et al makes use of coils through which the rods are caused to pass. The coils are powered by current at high frequency. Analyzing the voltage across the terminals of the coils and representing the impedance thereof makes it possible to evaluate tube wear.

That solution gives results which are satisfactory so long as the tubes are homogeneous, e.g. being made of stainless steel. However, it is no longer reliable if it uses conventional coils and the tubes have respective outer surface layers whose magnetic or electrical characteristics are significantly different from those of the bulk of the metal, e.g. because the tubes have been subjected to surface treatment for the purpose of reducing wear.

This applies in particular when the tubes are made of steel and have a surface layer that is 10 µm thick to several tens of µm thick, either of chromium which has electrical conductivity that is about six times greater than that of the base metal, or that is enriched in nitrogen obtained by electrical discharge in a rarified atmosphere containing nitrogen (ionic nitriding) and which is ferromagnetic.

SUMMARY OF THE INVENTION

The invention seeks in particular to provide a method and apparatus for inspection that satisfies practical requirements better than previously known methods and apparatus.

To this end, the invention provides, in particular, inspection apparatus comprising a measurement head having a measurement coil for surrounding the tube and means for powering the coil with voltage at high frequency, greater than 100 kHz, and for analyzing the impedance of the coil, the apparatus being characterized in that said head contains at least one magnet surrounding the coil and magnetic flux guides of material having high metallic permeability, on either side of the coil in the axial direction and co-operating with the magnet to constitute a magnetic circuit that creates a magnetic field whose maximum intensity lies inside the coil and close thereto.

In an advantageous embodiment, each of the guides is in the form of a ring having an external portion bearing against an end face of the magnet, and an internal portion converging towards the other guide and terminating in the immediate vicinity of the coil and substantially at the same level as the coil in the radial direction.

Generally, said means comprise an oscillator enabling the coil to be powered at a frequency that is variable in the range 100 kHz to at least 4 MHz.

In another aspect, the invention also provides a method of using eddy currents to inspect magnetic tubes having, on their outside faces, respective thin layers of magnetic or electrical characteristics that are different from those of the metal in depth, in which a coil surrounding the tube is powered by a voltage at high frequency lying in the range 100 kHz to 500 kHz in order to detect internal clearance, and at a higher frequency, and the part of the tube within the coil is simultaneously subjected to a continuous magnetic field that is of sufficient strength to saturate said thin layer magnetically, and the voltage across the terminals of the coil is analyzed.

In addition, the invention also seeks to make it possible to use eddy currents during a single measurement ass or two successive measurement passes, to detect variations along the tube in the clearance that exists between the tube and the material it contains.

For that purpose, the power supply means are designed to power the coil at the first frequency to detect internal clearance between the absorbent materials and the tube, and at a second frequency, greater than 4 MHz, to detect geometrical variations of the tube and cracks of the tube.

Such apparatus is particularly suitable for inspecting rods comprising a steel outer tube having a nitrided or chromium-plated surface layer and containing a column of absorbent material.

The measurement coil may be placed in conventional manner in one of the branches of a Wheatstone bridge whose other branch includes a reference coil (18) surrounding a length of standard tube. One of the diagonals of the bridge is connected to the high frequency power supply means and the other diagonal is connected via an amplifier to a demultiplexer feeding two load circuits each operating at a different frequency.

The above characteristics and others appear more clearly on reading the following description of a particular embodiment, given by way of non-limiting example. The description refers to the accompanying drawings.

BRIEF DESCRIPTION OF THE DRAWINGS

FIG. 1 is a theoretical diagram showing a setup for inspecting a tube by eddy currents;

FIG. 2 shows an eddy current measurement head constituting a particular embodiment of the invention;

FIG. 3 is a diagrammatic section view of the bottom portion of a control cluster rod containing absorbent material, showing the existence of two different clearances; and FIG. 4 is a perspective view showing a possible distribution for the measurement heads in apparatus for inspecting the cladding tubes of rods in a nuclear reactor control cluster.

DETAILED DESCRIPTION OF THE DRAWINGS

Conventionally, a tube 10 is inspected by eddy currents by comparing the tube 10 with a reference length of tube or standard 12, that does not have any defects, and as shown in FIG. 1. The tube 10 to be inspected is moved along a head containing a measurement coil 16 placed in one branch of a Wheatstone bridge 14 having a diagonal powered with AC at high frequency. The other branch of the bridge contains a reference coil 18 surrounding the standard length of tube 12. The measurement voltage is taken from the other diagonal of the bridge and it is applied to a measurement differential amplifier 21 whose output is digital, and it is then processed by a computer member 23.

A plurality of measurement coils can share a common reference coil by way of appropriate connection circuits.

To detect faults in thin steel tubes, the bridge is generally powered with an alternating voltage at a frequency lying in the range several hundreds of kHz and a few MHz.

To avoid problems posed by the existence of a surface layer or film having characteristics different from those of the base metal, the measurement head may have the structure shown in FIG. 2. The coil 14 is wound around a protection tube 17 in a coil support 19. It is enclosed in a body 20 which may be made of insulating material and which contains an annular magnet 22. The magnetic circuit of this magnet is closed by two flux guides 24 of material having high magnetic permeability, even at high inductance, e.g. ferrite.

Each of the two guides is ring-shaped. Each has an internal portion and an external portion in the form of a disk bearing against the end edge of the annular magnet 22. The internal portion converges towards the other guide and is itself terminated in the immediate vicinity of the coil and substantially at the same level in the radial direction. A gap remains between the internal portions. The width of the gap is at least equal to that of the coil.

The head also includes elements for protecting the coil 14 in the event of a deformed or swollen tube passing and for centering the tube.

In the case shown in FIG. 2, these elements comprise two centering brushes 26, e.g. made of slightly flexible plastics material and mounted in a ring 28 that is rigid, e.g. being made of stainless steel. Each ring 28 may have an internal rim 30 of diameter that is slightly greater than the nominal diameter of the tube to be inspected, thereby reducing the risk of the coil being damaged by a swollen zone of the tube by stopping the tube.

The annular magnet 22 and the flux guides 24 are selected as a function of the characteristics of the surface layer, so as to saturate said layer magnetically. For example, if the tube is made of stainless steel with surface nitriding, then the magnet and the guides are selected so that the magnetic field in the immediate vicinity of the coil is maximal thereat.

This disposition makes it possible to concentrate flux in a small working volume while conserving a coil that is optimized for operation over a wide frequency band, e.g. running from 100 kHz to 4 MHz in the abovementioned case of stainless steel tubes having a nitrided outer film to a depth of 10 $\mu$m to 20 $\mu$m.

By way of example, inspection may be performed at a frequency f1 equal to about 4 MHz for the purpose of detecting cracks and abnormal wear, and at a frequency f2=400 kHz for detecting sudden variations in the clearance between the tube and a metal element that it contains (caused by the use of an element whose diameter is deliberately reduced locally) or progressive variations due to swelling.

Examination of the tubes at a relatively low frequency f2 makes it possible, for example, to detect the elevation of the transition between an absorbent column 32 of a first diameter, and an absorbent column 34 of another diameter, within a cladding tube 10 (FIG. 3). When powered at a frequency that is low enough for the eddy currents to penetrate deeply, the impedance of the measurement tube is a function of the clearance between the internal element and the tube. The relationship between the two can be determined by prior calibration on a reference tube containing an element whose diameter decreases in steps. The signal obtained at the low frequency is phase shifted by 90°, unlike the component of the output signal due to wear or to faults in the cladding.

An elevation sensor, e.g. comprising a wheel 40 bearing against the rod or against another rod that moves together therewith, can be used to measure the displacement of the tube 10 and thus to determine the locations of faults in the longitudinal direction starting from the terminal bullet-shaped end 36 of a cladding tube, and also the locations of transitions between clearance j1 and clearance j2. A tube can be examined simultaneously at two frequencies f1 and f2 by injecting both frequencies simultaneously into the bridge 16 and then separating them at the output from the amplifier 20 by using a demultiplexer.

It is also possible to perform measurement at a third frequency lying between f1 and f2. By comparison with reference signals obtained on lengths having wear and defects of known type, the resulting signal can be used to determine the nature of the defects detected at the frequency f1.

The invention is particularly suitable for inspecting the cladding tubes of rods in a nuclear reactor control cluster, by using equipment of the kind described in document FR-A-2 585 869. To inspect the twenty-four rods of a single control cluster in two passes only, the apparatus may be designed to inspect twelve rods at a time. The heads containing the twelve measurement coils 14 are placed on a jig 42 (FIG. 4). The jig is fixed on a frame 44 carrying the reference coils 18 threaded over one, two, or three lengths of tube. A cover 46 includes tubular extensions that are inserted in the measurement heads and that serve to center the tubes while they are moving. The measurement heads are mounted movably relative to the jig 42 so as to accommodate rods that are offset from their nominal positions.

A group of twelve rods of a control cluster, or more generally a group of n/m rods (where n is the total number of rods in the cluster and m is an integer submulitple of n) can be analyzed as follows.

The signal processing member has as many channels as there are rods to be inspected simultaneously, and the channels are calibrated initially. Thereafter the cluster is caused to move so that the full lengths of its rods pass through the measurement coils while they are powered at least at the first frequency f1. The digitized values of the output voltages from the measurement bridges are recorded together with the elevation of the rods, as measured on only one of them. By analyzing the recorded output signals in differed time, it is possible to determine the wear rate at all levels and to determine which zones of the rods need to be inspected more thoroughly, e.g. by ultrasound. Such ultrasound examination can be performed using a moving measurement head that can be engaged on the path of any of the rods that is not being examined by eddy currents, and may comprise a probe capable of rotating about the rod in a probe carrier in order to map the periphery thereof at a given level.

In a variant embodiment, ultrasound examination is performed simultaneously with eddy current examination, but the signals obtained from the ultrasound examination are analyzed only in zones that are indicated as being doubtful by the eddy current examination.

The levels of transitions between clearances can be determined either simultaneously or separately. In general, it suffices to determine the locations of transitions on a fraction only of the rods (often the bottom portion).

We claim:

1. An apparatus for eddy current inspection of a metal tube having a thin layer on a radially outer outside face thereof with magnetic or electrical characteristics that are different from those of inner layers of said metal tube, said apparatus comprising:
   (a) a measurement head having a measurement coil for surrounding the tube; and
   (b) means for powering said coil with electrical voltage at a high frequency, greater than 100 kHz, and for analyzing an impedance of said coil;

(c) wherein said head further contains magnet means surrounding said coil and magnetic flux guides (24) located on either side of said coil in an axial direction of said coil, co-operating with said magnet means and shaped to constitute a magnetic circuit that generates a magnetic field having a maximum intensity radially inside said coil and close to said coil.

2. Apparatus according to claim 1 wherein the head is in the form of a sleeve and carries brushes (26) at its axial ends for centering the tube within the head.

3. Apparatus according to claim 2, wherein each brush (26) is associated with a ring (28) pierced by a through hole of diameter slightly greater than the nominal diameter of the tubes to be examined so as to protect the coil and the guides against insertion of a swollen tube.

4. Apparatus according to claim 1, wherein said means comprise an oscillator enabling the coil to be powered at a frequency that is variable in the range 100 kHz to at least 4 MHz.

5. Apparatus according to claim 4, for inspecting the rods of a nuclear reactor control cluster, each of said rods comprising a steel outer tube (10) having a nitrided surface layer and containing a column of absorbent material, wherein said means is provided for powering the coil:

at a first frequency lying in the range 100 kHz to 500 kHz to detect internal clearances between the absorbent materials and the tube; and at a second frequency greater than 4 MHz for detecting geometrical variations in the tube and cracks in the tube.

6. A Apparatus according to claim 4, wherein said means are provided for powering the coil at a third frequency lying between the first two frequencies.

7. Apparatus according to claim 4, wherein said coil is placed in one of the branches of a Wheatstone bridge whose other branch includes a reference coil (18) surrounding a length of standard tube (12), in that one of the diagonals of the bridge is connected to means for powering it at high frequency, and in that the other diagonal is connected via an amplifier (20) to a demultiplexer feeding two load circuits each operating at a different frequency.

8. Apparatus according to claim 1, wherein a plurality of measurement heads each for examining one rod are movably mounted relative to a common jig.

9. A method of eddy current inspection of a metal tube having a thin radially outer layer of a magnetic of electrical characteristics that are different from those of the metal of the tube under the thin layer, comprising the steps of:

(a) locating an annular coil around a radially outer annular zone of said layer on the metal tube;

(b) energizing said coil by a voltage at a frequency exceeding 100 kHz and simultaneously subjecting only that part of the tube which is radially inside the coil and in an immediate vicinity of said coil to a concentrated DC magnetic field of sufficient srength to saturate said thin layer; and (c) analyzing the voltage across terminals of the coil to measure an impedance of said coil.

10. The method according to claim 9, wherein at step (c) variations in the voltage are recorded responsive to displacement of said tube in order to determine doubtful zones, and comprising an additional step of subjecting doubtful zones to examination by ultrasounds.

11. An apparatus for eddy current inspection of a metal tube, comprising:

(a) a measurement head having a measurement coil for surrounding the tube; and (b) means for powering said coil with electrical voltage at a frequency greater than 100 kHz and for analyzing an impedance of said coil;

wherein said head further contains an annular magnet radially outwardly surrounding said coil and a pair of magnetic flux guides located each on one side of said coil in an axial direction of said coil and co-operating with said magnet to constitute a magnetic circuit that generates a magnetic field having a maximum value inside said coil, each of the flux guides being in the form of a ring having a radially external disk shaped portion bearing against a respective end surface of the magnet and an internal portion converging towards the other flux guide and axially terminating in the immediate vicinity of the coil substantially at a same radial level as the coil.

12. A method of eddy current inspection of a stainless steel tube cladding of a rod in a nuclear reactor control cluster having a thin radially outer layer whose magnetic or electrical characteristics are different from those of stainless steel, said method comprising the steps of:

(a) locating a coil around a part of said metal tube;

(b) energizing said coil by a voltage at a frequency exceeding 100 kHz, and simultaneously subjecting a zone of said thin layer which is located radially inside said coil to a DC magnetic field having a strength in said zone of said thin layer sufficient to saturate said zone of said thin layer magnetically, said magnetic field having a radial variation such that it has a value which is maximum close to said coil and within said thin layer; and (c) analyzing a voltage across terminals of said coil to measure an impedance of said coil.

* * * * *